US011014866B2

(12) United States Patent
Hatanpää et al.

(10) Patent No.: US 11,014,866 B2
(45) Date of Patent: *May 25, 2021

(54) SYNTHESIS AND USE OF PRECURSORS FOR VAPOR DEPOSITION OF TUNGSTEN CONTAINING THIN FILMS

(71) Applicant: ASM IP Holding B.V., Almere (NL)

(72) Inventors: Timo Hatanpää, Espoo (FI); Miika Mattinen, Helsinki (FI); Mikko Ritala, Espoo (FI); Markku Leskelä, Espoo (FI)

(73) Assignee: ASM IP Holding B.V., Almere (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/434,834

(22) Filed: Jun. 7, 2019

(65) Prior Publication Data

US 2019/0300468 A1    Oct. 3, 2019

Related U.S. Application Data

(63) Continuation of application No. 15/729,210, filed on Oct. 10, 2017, now Pat. No. 10,358,407.

(60) Provisional application No. 62/424,311, filed on Nov. 18, 2016, provisional application No. 62/407,168, filed on Oct. 12, 2016.

(51) Int. Cl.
| | | |
|---|---|---|
| *C07C 49/92* | (2006.01) | |
| *C07C 45/77* | (2006.01) | |
| *C23C 16/30* | (2006.01) | |
| *C23C 16/455* | (2006.01) | |

(52) U.S. Cl.
CPC .............. *C07C 49/92* (2013.01); *C07C 45/77* (2013.01); *C23C 16/305* (2013.01); *C23C 16/45553* (2013.01)

(58) Field of Classification Search
None
See application file for complete search history.

(56) References Cited

U.S. PATENT DOCUMENTS

| | | |
|---|---|---|
| 3,429,903 A | 2/1969 | Larson |
| 3,784,631 A | 1/1974 | Menapace et al. |
| 5,028,724 A | 7/1991 | Ivankovits et al. |
| 6,110,529 A | 8/2000 | Gardiner et al. |

(Continued)

FOREIGN PATENT DOCUMENTS

| | | |
|---|---|---|
| CN | 101117308 | 2/2008 |
| CN | 101343732 | 1/2009 |

(Continued)

OTHER PUBLICATIONS

Park et al. J. Phys. Chem. C 2012, 116, 25, 13480-13487.*

(Continued)

*Primary Examiner* — Clinton A Brooks
(74) *Attorney, Agent, or Firm* — Knobbe, Martens, Olson & Bear LLP

(57) ABSTRACT

Methods are provided for synthesizing W(IV) beta-diketonate precursors. Additionally, methods are provided for forming W containing thin films, such as $WS_2$, $WN_x$, $WO_3$, and W via vapor deposition processes, such as atomic layer deposition (ALD) type processes and chemical vapor deposition (CVD) type processes. Methods are also provided for forming 2D materials containing W.

20 Claims, 8 Drawing Sheets

(56) References Cited

U.S. PATENT DOCUMENTS

| | | | |
|---|---|---|---|
| 6,126,996 | A | 10/2000 | Kirlin et al. |
| 6,258,157 | B1 | 7/2001 | Gordon |
| 8,142,847 | B2 | 3/2012 | Shenai-Khatkhate et al. |
| 8,188,464 | B2 | 5/2012 | Quick |
| 9,802,220 | B2 | 10/2017 | Heys et al. |
| 9,911,590 | B2 | 3/2018 | Dussarrat et al. |
| 10,131,984 | B2 | 11/2018 | Okada |
| 2003/0008072 | A1 | 1/2003 | Lee et al. |
| 2004/0043557 | A1 | 3/2004 | Haukka et al. |
| 2004/0224504 | A1 | 11/2004 | Gadgil |
| 2008/0102205 | A1 | 5/2008 | Barry et al. |
| 2015/0211112 | A1 | 7/2015 | Cadot et al. |
| 2016/0122868 | A1 | 5/2016 | Kim et al. |

FOREIGN PATENT DOCUMENTS

| | | |
|---|---|---|
| CN | 101500989 | 8/2009 |
| CN | 101982562 | 3/2011 |
| CN | 104561937 | 4/2015 |
| EP | 1983073 | 10/2008 |
| JP | 2009-542654 | 12/2009 |
| JP | 2011-246466 | 12/2011 |
| JP | 2012-99594 | 5/2012 |
| KR | 1020080021709 | 3/2008 |
| KR | 1020090007245 | 1/2009 |
| KR | 101464173 | 11/2014 |
| WO | WO 96/40690 | 12/1996 |
| WO | WO 0218394 | 3/2002 |
| WO | WO 2008/002546 | 1/2008 |
| WO | WO 2010/114386 | 10/2010 |
| WO | WO 2015016412 | 2/2015 |
| WO | WO 2015/056944 | 4/2015 |

OTHER PUBLICATIONS

Baxter et al., "Chemical vapour deposition of electrochromic tungsten oxide films employing volatile tungsten(vl) 0x0 alkoxide/β-diketonate complexes", Chem. Commun., 1996, pp. 1129-1130.

Bonsu et al., "Synthesis and evaluation of κ2-β-diketonate and β-ketoesterate tungsten(vi) oxo-alkoxide complexes as precursors for chemical vapor deposition of $WO_x$ thin films", Dalton Trans., 2016, 45, pp. 10897-10908.

Browning et al., "Atomic layer deposition of $MoS_2$ films", Mater. Res. Express 2, 2015, 6 pages.

Buono-Core et al., "Synthesis and evaluation of bis-β-diketonate dioxotungsten(VI) complexes as precursors for the photodeposition of $WO_3$ films", Polyhedron, 30, 2011, pp. 201-206.

Chisholm et al., "The Molybdenum-Molybdenum Triple Bond. 13.[1] Preparations and Characterization of Bis(P-diketonato)tetraalkoxydimolybdenum and -ditungsten Compounds", Inorg. Chem., 1984, 23, pp. 613-618.

Chisholm et al., "Reactions of Metal-Metal Multiple Bonds. 11.[1] A Comparison of the Reactivity of $M_2(OR)_6$ (M=M) and $M_2(OR)_4(R'COCHCOR')_2$ (M=M) Compounds (M=Mu, W) with the π-Acid Ligands CO, RC=CR, and RNC", Inorg. Chem., 1984, 23, pp. 1037-1042.

Chisholm et al., "Attempts to prepare $W_2(β-diketonate)_4(M^4-M)$ complexes by reductive elimination from $d^3-d^3$ ditungsten complexes. Preparation and structures of $W_2 R_2(NMe_2)_2$ ($Bu^t$-acac)$_2$ and $W_2 R_2(OPr^i)_2$ ($Bu^t$-acac)$_2$ compounds, where R=Et, Ph, $CH_2$Ph, and $BC^{i}$", Journal of Cluster Science, Mar. 1994, vol. 5, Issue 1, pp. 67-82.

Doyle, Gerald, "The Reaction of Some Molybdenum and Tungsten Halides with .beta.-Diketones", Inorganic Chemistry, vol. 10, No. 10, 1971, pp. 2348-2350.

International Search Report and Written Opinion for International Application No. PCT/US2016/033955, Notification dated Oct. 18, 2016.

Kang et al., "High-mobility three-atom-thick semiconducting films with wafer-scale homogeneity", Nature, Apr. 30, 2015, vol. 520, pp. 656-660.

Mazurenko et al., "Synthesis, thermal stability, and IR and UV spectra of molybdenum and tungsten β-diketone complexes", Probl. Khim. Primen. β [Beta]-Diketonatov Met., [Mater. Vses. Semin.] (1982).

Zelazowlska et al., "$WO_3$-based electrochromic system with hybrid organic-inorganic gel electrolytes", Journal of Non-Crystalline Solids, 354, 2008, pp. 4500-4505.

* cited by examiner

SYNTHESIS AND USE OF PRECURSORS FOR VAPOR DEPOSITION OF TUNGSTEN CONTAINING THIN FILMS

CROSS-REFERENCE TO RELATED APPLICATIONS

The present application is a continuation of U.S. application Ser. No. 15/729,210, filed Oct. 10, 2017, which claims priority to U.S. Provisional Application No. 62/407,168, filed Oct. 12, 2016 and U.S. Provisional Application No. 62/424,311, filed Nov. 18, 2016 and is related to PCT Application No. PCT/US2016/033955 filed on May 24, 2016, each of which is hereby incorporated by reference.

PARTIES OF JOINT RESEARCH AGREEMENT

The invention claimed herein was made by, or on behalf of, and/or in connection with a join research agreement between the University of Helsinki and ASM Microchemistry Oy. The agreement was in effect on and before the date the claimed invention was made, and the claimed invention was made as a result of activities undertaken within the scope of the agreement.

FIELD

The present application relates generally to precursors and methods for forming thin films comprising tungsten by atomic layer deposition. Such films may find use, for example, as two-dimensional (2D) materials in electronic devices.

BACKGROUND

Transition metal dichalcogenide materials, especially 2D transition metal dichalcogenide materials such as W dichalcogenides have desirable electronic properties for a variety of applications. Additionally, unlike graphene, another two-dimensional material, certain two-dimensional transition metal dichalcogenides have a direct band gap and are semiconducting.

SUMMARY

In some aspects, processes for forming a W containing thin film are provided. In some embodiments a W containing thin film is formed on a substrate in a reaction chamber in a process comprising at least one cycle, the cycle comprising contacting the substrate with a vapor phase W precursor such that at most a molecular monolayer of W containing species is formed on the substrate surface, contacting the substrate with a vapor phase second precursor, and optionally repeating the two contacting steps until a W containing thin film of the desired thickness is formed. In some embodiments the W in the W precursor has an oxidation state of +IV. In some embodiments the second precursor reacts with the W containing species on the substrate surface.

In some embodiments the process is an atomic layer deposition (ALD) process. In some embodiments the process is a chemical vapor deposition (CVD) process. In some embodiments the process comprises two or more sequential cycles. In some embodiments the W containing thin film is a tungsten oxide, for example $WO_3$, tungsten nitride, for example $WN_x$, tungsten silicide, tungsten carbide, tungsten chalcogenide, for example $WS_2$, or elemental tungsten thin film, or mixtures thereof. In some embodiments the W containing film is a tungsten sulfide, tungsten selenide or tungsten telluride film. In some embodiments the W containing film may be a metallic film, a conducting film, or an insulating film. In some embodiments the oxidation state of the W in the W precursor is +IV. In some embodiments the W precursor is tetrakis(2,2,6,6-tetramethyl-3,5-heptanedionato)tungsten(IV), also referred to as $W(thd)_4$. In some embodiments the second precursor comprises a chalcogenide and may be, for example, $H_2S$, $H_2Se$, $H_2Te$, $(CH_3)_2S$, $(CH_3)_2Se$ or $(CH_3)_2Te$ In some aspects, atomic layer deposition (ALD) processes for forming a W containing thin film are provided. According to some embodiments, a W containing thin film is formed on a substrate in a reaction chamber in an ALD process comprising at least one cycle, the cycle comprising contacting the substrate with a vapor phase W precursor such that at most a molecular monolayer of W containing species is formed on the substrate surface, removing excess W precursor and reaction byproducts, if any, contacting the substrate with a vapor phase second precursor, removing excess second precursor and reaction byproducts, if any, and repeating the contacting and removing steps until a W containing thin film of the desired thickness is formed. In some embodiments the W precursor may comprise a W(IV) beta-diketonate compound. In some embodiments the second precursor reacts with the W containing species on the substrate surface.

In some embodiments, chemical vapor deposition (CVD) processes for forming a W containing thin film are provided. According to some embodiments a W containing thin film is formed on a substrate in a reaction chamber in an CVD process comprising at least one cycle, the cycle comprising contacting the substrate with a vapor phase W precursor pulse. In some embodiments the cycle can also comprise contacting the substrate with a vapor phase second precursor pulse, and repeating the contacting steps until a W containing thin film of the desired thickness is formed. In some embodiments the W precursor pulse and the second precursor pulse may be partially overlapping pulses. In some embodiments a precursor or precursors may decompose away from the substrate surface. In some embodiments the W precursor may comprise a W(IV) beta-diketonate. In some embodiments the vapor deposition processes for forming a W containing thin film may comprise a pulsed CVD process, or a sequential CVD process.

In some aspects, atomic layer deposition (ALD) processes for forming a W sulfide, such as $WS_2$, tungsten selenide, or tungsten telluride 2D material are provided. According to some embodiments, a W sulfide, selenide, or telluride 2D material is formed on a substrate in a reaction chamber in an ALD process comprising at least one cycle, the cycle comprising contacting the substrate with a vapor phase W precursor such that at most a molecular monolayer of W containing species is formed on the substrate surface, removing excess W precursor and reaction byproducts, if any, contacting the substrate with a vapor phase sulfur, selenium, or tellurium precursor, and removing excess sulfur, tellurium or selenium precursor and reaction byproducts, if any. In some embodiments the W precursor is a W(IV) beta-diketonate precursor. In some embodiments the sulfur, selenium, or tellurium precursor reacts with the W containing species on the substrate surface.

In some aspects, processes for forming a W sulfide, selenide, or telluride 2D material are provided. According to some embodiments, a W sulfide, selenide, or telluride 2D material is formed on a substrate in a reaction chamber in an cyclic process comprising at least one cycle, the cycle comprising contacting the substrate with a vapor phase W precursor such that at most a monolayer, less than or equal to about 50% of a monolayer, less than about 25% of a monolayer, or less than about 10% of a monolayer of W containing material is formed on the substrate surface; exposing the substrate to purge gas and/or removing excess W precursor and reaction byproducts, if any; contacting the substrate with a vapor phase sulfur, selenium, or tellurium precursor; and exposing the substrate to purge gas and/or removing excess sulfur, tellurium or selenium precursor and reaction byproducts, if any. In some embodiments the W precursor is a W(IV) beta-diketonate precursor. In some embodiments the sulfur, selenium, or tellurium precursor reacts with the W containing material deposited on the substrate surface.

In some embodiments the W containing thin film is a W sulfide, selenide, or telluride thin film, for example a $WS_2$ thin film. In some embodiments the oxidation state of the W atom comprising the W precursor is +IV. In some embodiments the chalcogen precursor comprises $H_2S$, $H_2Se$, $H_2Te$, $(CH_3)_2S$, $(CH_3)_2Se$, $(CH_3)_2Te$, or $(R_3Si)_2E$, where R is a hydrocarbon group and E is S, Se or Te. In some embodiments the W precursor is $W(thd)_4$ and the chalcogen precursor is $H_2S$. In some embodiments the 2D material comprises $WS_2$.

In some embodiments the W containing thin film is a tungsten nitride ($WN_x$), tungsten oxide ($WO_3$), or W thin film. In some embodiments the W containing film comprises $WN_x$, $WO_3$, $WS_2$, W, and/or some combination of the same. In some embodiments $WN_x$ thin films may be used in microelectronics, for example as a contact material, as a conductive layer, or as a barrier layer between silicon and other metals, for example tungsten or copper. In some embodiments $WO_3$ thin films may be used for X-ray screen phosphor, in gas sensors, or in different electrochromic devices.

In some aspects, methods for making W(IV) beta-diketonate precursors are provided. In some embodiments a W(IV) beta-diketonate precursor is formed by forming a first product by reacting an alkali metal compound with a beta-diketone compound in a solvent, adding a W(IV) halide to a solvent to form a W(IV) halide solution, and subsequently adding the first product to the W(IV) halide solution. In some embodiments a W(IV) beta-diketonate precursor having the formula $W(L)_4$ is formed, wherein L is a beta-diketonato ligand. In some embodiments L comprises tfac, hfac, fod or acac. In some embodiments the process for making a W(IV) beta-diketonate precursor can comprise forming a first product by reacting KH with Hthd in THF, adding $WCl_4$ to THF to form a $WCl_4$ solution, and subsequently adding the first product to the $WCl_4$ solution to thereby form a W(IV) beta-diketonate precursor having the formula tetrakis(2,2,6,6-tetramethyl-3,5-heptanedionato)tungsten(IV), or $W(thd)_4$.

In some aspects, processes for forming a W containing material are provided. According to some embodiments, a W containing material is formed on a substrate in a reaction chamber by a process comprising at least one deposition cycle, the cycle comprising alternately and sequentially contacting the substrate with a vapor phase W precursor and a vapor phase second precursor. In some embodiments the W in the W precursor has an oxidation state of +IV.

In some embodiments the deposition is repeated two or more times. In some embodiments excess W precursor and reaction byproducts, if any, are removed subsequent to contacting the substrate with a vapor phase W precursor and prior to contacting the substrate with the vapor phase second precursor. In some embodiments excess second precursor and reaction byproducts, if any, are removed subsequent to contacting the substrate with a vapor phase second precursor and prior to beginning another deposition cycle. In some embodiments the substrate is contacted with a purge gas subsequent to contacting the substrate with the W vapor phase precursor and prior to contacting the substrate with the vapor phase second precursor. In some embodiments the substrate is contacted with a purge gas subsequent to contacting the substrate with the second vapor phase precursor and prior to beginning another deposition cycle. In some embodiments the W containing material comprises elemental W. In some embodiments the W containing material comprises a W oxide material, for example $WO_3$. In some embodiments the W containing material comprises a W nitride material, for example $WN_x$. In some embodiments the W containing material comprises a W chalcogenide material, for example $WS_2$. In some embodiments the W containing material comprises a W silicide material.

BRIEF DESCRIPTION OF THE DRAWINGS

The invention will be better understood from the Detailed Description and from the appended drawings, which are meant to illustrate and not to limit the invention, and wherein.

DETAILED DESCRIPTION

Figure 1:
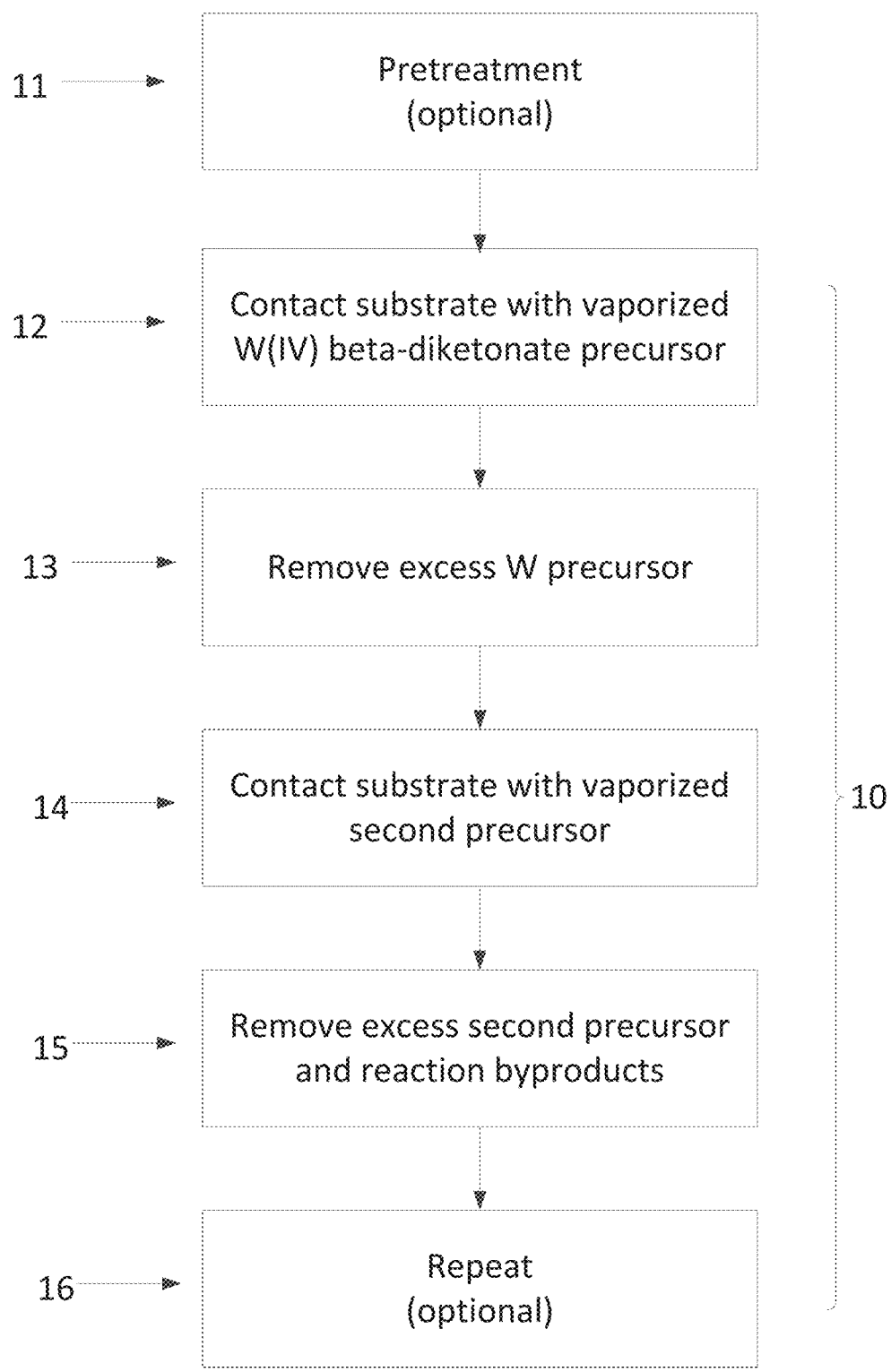
FIG. 1 is a process flow diagram generally illustrating a method for depositing a W containing thin film.

As discussed below, W containing thin films can be deposited on a substrate by vapor deposition type processes, such as atomic layer deposition (ALD) and chemical vapor deposition (CVD) type processes. In some embodiments W containing films such as tungsten oxide, for example $WO_3$; tungsten nitride, for example $WN_x$; tungsten chalcogenide, for example $WS_2$; tungsten silicide; and/or elemental tungsten films can be deposited on a substrate by a vapor deposition process, for example an ALD or CVD type process. In some embodiments W chalcogenide thin films, particularly W sulfide or selenide thin films can be deposited on a substrate by ALD or CVD type processes.

Suitable substrate materials may include insulating materials, dielectric materials, crystalline materials, epitaxial, heteroepitaxial, or single crystal materials such as oxides. For example, the substrate may comprise $Al_2O_3$, sapphire, silicon oxide, or an insulating nitride, such as AlN. Further, the substrate material and/or substrate surface may be selected by the skilled artisan to enhance, increase, or maximize two-dimensional crystal growth thereon. In some embodiments the substrate surface on which the W containing thin film or material is to be deposited does not comprise semiconductor materials, such as Si, Ge, III-V compounds, for example GaAs and InGaAs, or II-VI compounds. In some embodiments the substrate surface on which the W containing thin film or material is to be deposited may also comprise materials other than insulating materials. In some embodiments, after deposition of the W containing thin film, the W containing thin film is removed from at least a portion of the substrate comprising a material other than an insulating material. In some embodiments the substrate surface on which the W containing thin film or material, such as a W chalcogenide thin film or material, is to be deposited comprises a chalcogen, such as sulfur, selenium or tellurium. In some embodiments the substrate surface on which the W containing thin film or material is to be deposited comprises surface groups which comprise a chalcogen, such as surface groups having chalcogen-hydrogen bonds, such as a —S—H group.

ALD type processes are based on controlled surface reactions of precursor chemicals. Gas phase reactions are avoided by alternately and sequentially contacting the substrate with the precursors. Vapor phase reactants are separated from each other on the substrate surface, for example, by removing excess reactants and/or reactant byproducts from the reaction chamber between reactant pulses.

CVD type processes typically involve gas phase reactions between two or more reactants. The reactants can be provided simultaneously to the reaction space or substrate. The substrate or reaction space can be heated to promote the reaction between the gaseous reactants. CVD deposition occurs when the reactants or precursors are provided to the reaction space or substrate. In some embodiments the reactants are provided until a thin film having a desired thickness is deposited. In some embodiments cyclical CVD type processes can be used with multiple cycles used to deposit a thin film having a desired thickness. In some embodiments one or more plasma reactants can be used in the CVD process.

In some embodiments an ALD-process can be modified to be a partial CVD processes. In some embodiments a partial CVD process can include at least partial decomposition of one or more precursors. In some embodiments ALD processes can be modified to be a pulsed CVD processes. In some embodiments an ALD process is modified to use overlapping or partially overlapping pulses of reactants. In some embodiments an ALD process is modified to use extremely short purge or removal times, such as below 0.1 s (depending on the reactor). In some embodiments an ALD process is modified to use extremely long or continuous pulse times. For example, in some embodiments an ALD process is modified to use no purge or removal at all after at least one pulse. In some embodiments no purge is used after a W precursors pulse. In some embodiments no purge is used after an second precursor pulse. In some embodiments no purge is used after either a W precursor pulse or a second precursor pulse.

In some embodiments a single W precursor is utilized. Thus, in some embodiments the process may not include contacting the substrate with a vapor phase second reactant. In some embodiments a substrate is exposed to one precursor pulse, or sequential precursor pulses separate by a precursor removal or purge step. For example, in some embodiments a substrate may be continuously or intermittently contacted with a vapor phase W precursor and not with a vapor phase second reactant (or any additional reactants). Although in some embodiments a substrate may be contacted by another species that does not react, such as an inert purge gas or carrier gas, in addition to the vapor phase W precursor. In some embodiments a deposition process may include only one W precursor pulse.

In some embodiments the substrate may be contacted with a vapor phase W precursor. Subsequently, excess W precursor and reaction byproducts, if any, may be removed from the substrate surface, and the substrate may again be contacted with a vapor phase W precursor, for example in a sequential pulse. The W precursor may be the same in both pulses, or different. In some embodiments the substrate may not contacted with a second reactant, or any additional reactant. Although in some embodiments a substrate may be contacted by another species that does not react, such as an inert purge gas or carrier gas, in addition to the vapor phase W precursor.

Regarding ALD-type processes, briefly, a substrate is heated to a suitable deposition temperature, generally at lowered pressure. Deposition temperatures are generally maintained below the thermal decomposition temperature of the reactants but at a high enough level to avoid condensation of reactants and to provide the activation energy for the desired surface reactions. Of course, the appropriate temperature window for any given ALD reaction will depend upon the surface termination and reactant species involved. Here, the temperature varies depending on the type of film being deposited and particular precursors. In some embodiments the deposition temperature may be from about 50° C. to about 800° C., from about 100° C. to about 700° C., from about 200° C. to about 600° C., or from about 300° C. to about 500° C. In some embodiments the deposition temperature may be at or above about 100° C., at or above about 200° C., at or above about 300° C., or at or above about 350° C. or higher, for example up to about 1000° C. In some embodiments the deposition temperature may be up to about 1000° C., up to about 700° C., or up to about 600° C.

In some embodiments the deposition temperature may be above the decomposition temperature of a reactant. In some embodiments the deposition temperature is above the decomposition temperature of the W reactant but still low enough to maintain reasonably surface controlled growth of a film and a growth rate which is greater than 0 but less than or equal to about a monolayer of material per deposition cycle. In some embodiments a deposition cycle growth rate may be greater than 0 but less than or equal to about 50%, less than about 25%, or less than about 10% of about a complete monolayer of material being deposited per cycle. In some embodiments a complete monolayer is one in which all available reactive sites are occupied. In some embodiments the growth rate of ALD process is greater than 0 but less than about 2 Å/cycle, less than about 1 Å/cycle, less than about 0.5 Å/cycle, less than about 0.1 Å/cycle, less than about 0.05 Å/cycle or in some instances less than about 0.02 Å/cycle. In other embodiments the growth rate of process other than pure ALD may be more than about 0.02 Å/cycle, more than about 0.05 Å/cycle, more than about 0.1 Å/cycle, more than about 0.5 Å/cycle, more than about 1 Å/cycle, or more than about 2 Å/cycle or greater, up to a maximum growth rate as would be understood by the skilled artisan given the deposition conditions of the processes described herein.

In some embodiments a deposition process may not be a pure ALD process. In some embodiments a second precursor may flow continuously or substantially continuously through a reaction space throughout a deposition process. For example, the flow rate of a second precursor through a reaction space may be reduced while the substrate is contacted with a W precursor. In some embodiments where a second precursor may flow continuously, the growth rate of the film per cycle is greater than 0 but less than or equal to about one monolayer of the material being deposited. In some embodiments where the second precursor flows continuously, the growth rate per cycle is greater than 0 but less than or equal to about 50%, less than about 25%, or less than about 10% of a complete monolayer of the material being deposited.

The surface of the substrate is contacted with a vapor phase first reactant. In some embodiments a pulse of vapor phase first reactant is provided to a reaction space containing the substrate. In some embodiments the substrate is moved to a reaction space containing vapor phase first reactant. Conditions are typically selected such that no more than about one monolayer of W containing species from the first reactant is adsorbed on the substrate surface in a self-limiting manner. The appropriate contacting times can be readily determined by the skilled artisan based on the particular circumstances. Excess first reactant and reaction byproducts, if any, are removed from the substrate surface, such as by purging with an inert gas or by removing the substrate from the presence of the first reactant.

Purging means that vapor phase precursors and/or vapor phase byproducts are removed from the substrate surface such as by evacuating a chamber with a vacuum pump and/or by replacing the gas inside a reactor with an inert gas such as argon or nitrogen. Typical purging times are from about 0.05 to 20 seconds, between about 0.2 and 10, or between about 0.5 and 5 seconds. However, other purge times can be utilized if necessary, such as where highly conformal step coverage over extremely high aspect ratio structures or other structures with complex surface morphology is needed, or where different reactor types may be used, such as a batch reactor.

The surface of the substrate is contacted with a vapor phase second gaseous reactant or precursor. The second reactant may react with the W containing species from the first reactant that are present on the substrate surface. In some embodiments a pulse of a second gaseous reactant is provided to a reaction space containing the substrate. The vapor phase second gaseous reactant may be provided into the reaction chamber in a substantially continuous flow from a reaction chamber inlet to an outlet. In some embodiments outlet flow from the reaction chamber, for example a pump line, is not closed. In some embodiments outlet flow from the reaction chamber, for example flow from a reaction chamber to a pump line and further through the pump line prior to the pump, is not substantially closed, but may be restricted. In some embodiments the substrate is moved to a reaction space containing the vapor phase second reactant. Excess second reactant and gaseous byproducts of the surface reaction, if any, are removed from the substrate surface. In some embodiments there is no dwell time for the reactants. In some embodiments a vapor phase reactant is not static in the reaction space while the vapor phase reactant is contacting the substrate. A vapor phase reactant may be static when the reactant is not experiencing flow relative to the substrate, or when the reactant is flowing into the reaction space from one inlet, with no open outlet.

The steps of contacting and removing are repeated until a thin film of the desired thickness has been selectively formed on the substrate, with each cycle leaving no more than about a molecular monolayer. The steps of contacting and removing a first vapor phase W precursor may be referred to as a first precursor phase, a W precursor phase, or a W phase. The steps of contacting and removing a second vapor phase precursor may be referred to as a second precursor phase. Together, these two phases can make up a deposition cycle. Additional phases comprising alternately and sequentially contacting the surface of a substrate with other reactants can be included to form more complicated materials, such as ternary materials.

As mentioned above, in some embodiments each phase of each cycle may be generally self-limiting. In some embodiments an excess of reactant precursors is supplied in each phase to saturate the susceptible structure surfaces. Surface saturation ensures reactant occupation of essentially all available reactive sites (subject, for example, to physical size or "steric hindrance" restraints) and thus ensures excellent step coverage and uniformity. Typically, some material, but less than one molecular layer of material, is deposited with each cycle, however, in some embodiments more than one molecular layer is deposited during the cycle.

Removing excess reactants can include evacuating some of the contents of a reaction space and/or purging a reaction space with helium, nitrogen or another inert gas. In some embodiments purging can comprise turning off the flow of the reactive gas while continuing to flow an inert carrier gas to the reaction space.

The precursors employed in the ALD type processes may be solid, liquid or gaseous materials under standard conditions (room temperature and atmospheric pressure), provided that the precursors are in vapor phase before they are contacted with the substrate surface. Contacting a substrate surface with a vaporized precursor means that the precursor vapor is in contact with the substrate surface for a limited period of time. Typically contacting times are from about 0.05 to 20 seconds, between about 0.2 and 10, or between about 0.5 and 5 seconds. In some embodiments the vapor phase second gaseous contacting time is of the same order of magnitude as the vapor phase first gaseous reactant contacting time. In some embodiments the vapor phase second gaseous contacting time is no more than about 100 times longer than the vapor phase first gaseous reactant contacting time.

However, depending on the substrate type and its surface area, the contacting time may be even higher than 20 seconds. Contacting times can be on the order of minutes in some cases. The optimum contacting time can be determined by the skilled artisan based on the particular circumstances. In some embodiments the second precursor contacting time is greater than 0, but less than about 60 seconds, less than about 30 seconds, less than about 10 seconds, or less than about 5 seconds.

The mass flow rate of the precursors can also be determined by the skilled artisan. In some embodiments the flow rate of a W precursor is between about 1 and 1000 sccm without limitation, or between about 100 and 500 sccm.

The pressure in a reaction chamber is typically from about 0.01 to about 50 mbar, or from about 0.1 to about 10 mbar. However, in some cases the pressure will be higher or lower than this range, as can be determined by the skilled artisan given the particular circumstances.

Before starting the deposition of the film, the substrate is typically heated to a suitable growth temperature. The growth temperature varies depending on the type of thin film formed, physical properties of the precursors, etc. In some embodiments the growth temperature may be from about 50° C. to about 800° C., from about 100° C. to about 700° C., from about 200° C. to about 600° C., or from about 300° C. to about 500° C. In some embodiments the growth temperature may be at or above about 100° C., at or above about 200° C., at or above about 300° C., or at or above about 350° C. or higher, for example up to about 1000° C. In some embodiments the growth temperature may be up to about 1000° C., up to about 700° C., or up to about 600° C. In some embodiments the growth temperature may be above the decomposition temperature of the W precursor. For example, in some embodiments the growth temperature may be above the decomposition temperature of W(thd)$_4$.

The growth temperature can be less than the crystallization temperature for the deposited materials such that an amorphous thin film is formed or it can be above the crystallization temperature such that a crystalline thin film is formed.

In some embodiments the deposition temperature may vary depending on a number of factors such as, and without limitation, the reactant precursors, the pressure, flow rate, the arrangement of the reactor, crystallization temperature of the deposited thin film, and the composition of the substrate including the nature of the material to be deposited on. The specific growth temperature may be selected by the skilled artisan. It is to be noted that the thermal budget, that is a reaction temperature and optionally an anneal temperature, during deposition and at any point in further processing after the deposition for films of the present invention is can be less than about 800° C., less than about 650° C., less than about 600° C., or in some instances less than about 500° C., but above about 50° C.

In some embodiments the deposited W containing thin film may be subjected to optional post deposition treatment process. In some embodiments, for example, a post deposition treatment process may comprise an annealing process, for example a forming gas annealing process. In some embodiments a post deposition treatment process may comprise exposing the W containing thin film or material surface to a plasma In some other embodiments a post deposition treatment process does not comprise exposing the W containing thin film or material surface to a plasma.

Examples of suitable reactors that may be used include commercially available ALD equipment such as the F-120® reactor, Eagle® XP8, Pulsar® reactor and Advance® 400 Series reactor, available from ASM America, Inc. of Phoenix, Ariz., ASM Japan KK, Tokyo, Japan and ASM Europe B.V., Almere, Netherlands. In addition to these ALD reactors, many other kinds of reactors capable of ALD growth of thin films, including CVD reactors equipped with appropriate equipment and means for pulsing the precursors can be employed. In some embodiments a flow type ALD reactor is used. In some embodiments reactants are kept separate until reaching the reaction chamber, such that shared lines for the precursors are minimized. However, other arrangements are possible, such as the use of a pre-reaction chamber as described in U.S. patent application Ser. No. 10/929,348, filed Aug. 30, 2004 and Ser. No. 09/836,674, filed Apr. 16, 2001, the disclosures of which are incorporated herein by reference.

In some embodiments a suitable reactor may be a batch reactor and may contain more than about 25 substrates, more than about 50 substrates or more than about 100 substrates. In some embodiments a suitable reactor may be a mini-batch reactor and may contain from about 2 to about 20 substrates, from about 3 to about 15 substrates or from about 4 to about 10 substrates.

The growth processes can optionally be carried out in a reactor or reaction space connected to a cluster tool. In a cluster tool, because each reaction space is dedicated to one type of process, the temperature of the reaction space in each module can be kept constant, which improves the throughput compared to a reactor in which the substrate is heated up to the process temperature before each run.

A stand-alone reactor can be equipped with a load-lock. In that case, it is not necessary to cool down the reaction space between each run.

According to some embodiments, and illustrated in FIG. 1, a W containing thin film is formed on a substrate by an ALD type process comprising at least one deposition cycle 10 the deposition cycle comprising:

contacting the surface of a substrate with a vaporized W(IV) beta-diketonate precursor at step 12 to adsorb at most a molecular monolayer of W containing species on the substrate surface;

removing excess W precursor and reaction by products, if any, from the surface at step 13;

contacting the surface of the substrate with a vaporized second precursor at step 14, wherein the second precursor reacts with the W containing species on the substrate surface; and removing from the surface excess second precursor and any gaseous by-products formed in the reaction between the W precursor layer and the second precursor at step 15.

The contacting and removing steps can be repeated 16 until a W containing thin film of the desired thickness has been formed.

Although the illustrated deposition cycle begins with contacting the surface of the substrate with the W precursor, in other embodiments the deposition cycle begins with contacting the surface of the substrate with the second precursor. It will be understood by the skilled artisan that if the surface of the substrate is contacted with a first precursor and that precursor does not react then the process will begin when the next precursor is provided. In some embodiments, the reactants and reaction by-products can be removed from the substrate surface by stopping the flow of W precursor while continuing the flow of an inert carrier gas such as nitrogen or argon.

In some embodiments, the reactants and reaction by-products can be removed from the substrate surface by stopping the flow of second reactant while continuing the flow of an inert carrier gas. In some embodiments the substrate is moved such that different reactants alternately and sequentially contact the surface of the substrate in a desired sequence for a desired time. In some embodiments the removing steps are not performed. In some embodiments no reactant may be removed from the various parts of a chamber. In some embodiments the substrate is moved from a part of the chamber containing a first precursor to another part of the chamber containing the second precursor. In some embodiments the substrate is moved from a first reaction chamber to a second, different reaction chamber.

In some embodiments the deposited W containing film may comprise a tungsten oxide, for example WO$_3$, tungsten nitride, for example WN$_x$, tungsten chalcogenide, for example WS$_2$, tungsten silicide, and/or elemental tungsten thin film. In some embodiments the deposited W containing film may comprise a dichalcogenide thin film. In some embodiments the deposited thin film may comprise a tungsten dichalcogenide. In some embodiments the deposited thin film may comprise WS$_2$, WSe$_2$, or WTe$_2$. For simplicity, these dichalcogenides have been indicated to have these general stoichiometries, but it will be understood that the exact stoichiometry of any given W containing film or material will vary based on the oxidation state of the elements involved. Accordingly, other stoichiometries are expressly contemplated.

Although the term "dichalcogenide" is used herein and these dichalcogenides are indicated to have general stoichiometries with the ratio of metal atoms, such as W, to chalcogen atoms, such as S, Se, or Te, of 1:2, the stoichiometry of the films may vary. For example the ratio of metal atoms to chalcogen atoms may vary due to the analysis techniques used and/or the process conditions. In some embodiments the ratio of metal atoms to chalcogen atoms can be from about 1:3 to about 2:1, from about 1:2.5 to about 1:1, or from about to 1:2. In some embodiments the dichalcogenide film may contain from about 20 at-% to about 50 at-%, or from about 25 at-% to about 40 at-% of W. In some embodiments the dichalcogenide film may contain from about 30 at-% to about 75 at-%, or from about 35 at-% to about 70 at-% of a chalcogen (S, Se or Te).

In some embodiments the W containing dichalcogenide film may contain elements other than W and chalcogens. In some embodiments the W containing dichalcogenide film may contain a total of less than about 35 at-% of elements, including hydrogen, other than W and chalcogens, or total of less than about 25 at-%. In some embodiments the film may contain less than about 20 at-% carbon, less than about 15 at-% carbon, or less than about 10 at-% carbon. In some embodiments the film may contain less than about 15 at-% hydrogen, less than about 10 at-% hydrogen, or less than about 5 at-% hydrogen. In some embodiments the film may contain less than about 10 at-% oxygen, less than about 5 at-% oxygen, or less than about 3 at-% oxygen. In some embodiments the film may contain less than about 10 at-%, less than about 5 at-%, or less than about 3 at-% of elements other than W, chalcogens, hydrogen, carbon or oxygen. It is to be noted that a W containing film containing the above described elements may still be suitable for different applications, such as for a 2D-material.

In some embodiments the deposited W containing film may comprise additional elements other than W, chalcogens (S, Te or Se), oxygen, nitrogen, and/or silicon. In some embodiments the deposited W containing film may comprise a dopant. In some embodiments the deposited W containing film may comprise two or more of the elements of the group of chalcogens (S, Te or Se), oxygen, nitrogen or silicon. In some embodiments the deposited W chalcogenide containing film may comprise two or more of the elements of the group of chalcogens (S, Te or Se). In some embodiments the thin films of the present disclosure can include any number of metals. According to some embodiments W containing films may include two or more metals. In some embodiments, additional deposition phases are added to one or more deposition cycles to incorporate an additional metal or metals into a W containing thin film. An additional metal phase or phases may follow the first metal phase or follow the second phase, or may follow both phases. In some embodiments two or more different metal precursors may be provided simultaneously in the same metal phase of a deposition cycle. In some embodiments metal precursors comprising different metals may be used in different deposition cycles. For example, a first metal precursor may be the only metal precursor used in one or more deposition cycles and a second metal precursor comprising a second, different metal, may be used in one or more other deposition cycles.

Referring again to FIG. 1, some embodiments may include an optional pretreatment process at step 11 applied to the substrate surface. A pretreatment process may comprise one or more steps. In the pretreatment, the substrate surface on which W containing thin film is to be deposited may be exposed to one or more pretreatment reactants and/or to specific conditions, such as temperature or pressure. A pretreatment may be used for any number of reasons including to clean the substrate surface, remove impurities, remove native oxide, and provide desirable surface terminations. In some embodiments, a pretreatment comprises exposing the substrate surface to one or more pretreatment reactant, such as $(NH_4)_2S$, $H_2S$, HCl, HBr, $Cl_2$, or HF. In some embodiments, a pretreatment process is carried out at about the same temperature as the subsequent deposition process.

As described below, a number of different precursors can be used to deposit W containing thin films. In some embodiments the W precursor has a formula of $W(thd)_4$, wherein thd is 2,2,6,6-tetramethyl-3,5-heptanedionato. In some embodiments the second precursor is one of $H_2S$ or $H_2Se$. In some embodiments the W precursor is $W(thd)_4$, the second precursor is $H_2S$, and the resultant W containing thin film is a $WS_2$ thin film.

In some embodiments a $WS_2$ thin film is formed on a substrate by an ALD type process comprising at least one deposition cycle comprising:

contacting the surface of a substrate with vaporized $W(thd)_4$ to a at most a molecular monolayer of W containing species on the substrate;

removing excess $W(thd)_4$ and reaction by products, if any, from the surface;

contacting the surface of the substrate with vaporized $H_2S$; and removing from the surface excess $H_2S$ and any gaseous by-products formed in the reaction between the W containing species layer and the $H_2S$.

The contacting and removing steps can be repeated until a $WS_2$ thin film of the desired thickness has been formed.

In some embodiments a W containing thin film may be formed on a substrate by a vapor deposition process comprising contacting the substrate with a vaporized W(IV) beta-diketonate precursor. In some embodiments the process can optionally including contacting the substrate with a second precursor, such as a vapor phase second precursor. In some embodiments the vapor deposition process may be a chemical vapor deposition (CVD) process, a pulsed CVD process, a sequential CVD process, an ALD process, or any other type of chemical-reaction based vapor deposition process.

W Precursors

In some embodiments the W of the W precursor has an oxidation state of +IV. In some embodiments the W precursor may comprise four beta-diketonato ligands. In some embodiments the W precursor may comprise a W(IV) beta-diketonate compound. In some embodiments the W precursor does not comprise one or more halide ligands. In some embodiments the W precursor may comprise at least one beta-diketonate ligand. In some embodiments the W precursor may comprise at least one bidentate ligand which is bonded to W through at least one oxygen atom. In some embodiments the W precursor may comprise $W(acac)_4$ where acac is an acetylacetone ligand, $W(hfac)_4$ where hfac is a hexafluoroacetylacetone ligand, or $W(thd)_4$ where thd is a 2,2,6,6-tetramethyl-3,5-heptanedionato ligand. In some embodiments the W in the W precursor may comprise an oxidation state of +IV and may not be oxidized during the formation of the resultant thin film, whereupon the W has an oxidation state of +IV.

In some embodiments the W precursor is vaporized without solvent. In some embodiments the W precursor is not mixed with solvent, such as organic solvent.

In some embodiments W(IV) beta-diketonates may be used in vapor deposition type processes to deposit any kind of W containing thin film. In some embodiments W(IV) beta-diketonates may be used in ALD type processes to deposit any kind of W containing thin film. In some embodiments W(IV) beta-diketonates may be used in CVD type processes to deposit any kind of W containing thin film. In some embodiments W beta-diketonates may be used to deposit elemental W films, W sulfide films, W oxide films, W nitride films, or W silicide films. In particular, W(thd)$_4$ may be used in ALD and CVD type processes to deposit any kind of W containing thin film.

In some embodiments an elemental W thin film may be formed on a substrate by an ALD type process comprising at least one deposition cycle comprising:

contacting the surface of a substrate with vaporized W(IV) beta-diketonate precursor to form at most a molecular monolayer of W containing species on the substrate;

removing excess W(IV) beta-diketonate precursor and reaction by products, if any, from the surface;

contacting the surface of the substrate with a second reactant, such as H$_2$, or hydrogen plasma, radicals, or atoms; and removing from the surface excess second reactant and any gaseous by-products formed in the reaction between the W containing species layer and the second reactant.

The contacting and removing steps can be repeated until an elemental W thin film of the desired thickness has been formed.

In some embodiments a W oxide thin film may be formed on a substrate by an ALD type process comprising at least one deposition cycle comprising:

contacting the surface of a substrate with vaporized W(IV) beta-diketonate precursor to form at most a molecular monolayer of W containing species on the substrate;

removing excess W(IV) beta-diketonate precursor and reaction by products, if any, from the surface;

contacting the surface of the substrate with an oxygen precursor, such as water, ozone, or oxygen plasma, radicals, or atoms; and removing from the surface excess oxygen precursor and any gaseous by-products formed in the reaction between the W containing species layer and the oxygen precursor.

The contacting and removing steps can be repeated until a W oxide thin film of the desired thickness has been formed.

In some embodiments a W nitride thin film may be formed on a substrate by an ALD type process comprising at least one deposition cycle comprising:

contacting the surface of a substrate with vaporized W(IV) beta-diketonate precursor to form at most a molecular monolayer of W containing species on the substrate;

removing excess W(IV) beta-diketonate precursor and reaction by products, if any, from the surface;

contacting the surface of the substrate with a precursor comprising nitrogen; and removing from the surface excess nitrogen precursor and any gaseous by-products formed in the reaction between the W containing species layer and the precursor comprising nitrogen.

The contacting and removing steps can be repeated until a W nitride thin film of the desired thickness has been formed.

In some embodiments a suitable precursor comprising nitrogen may include NH$_3$. In some embodiments a suitable precursor comprising nitrogen may include nitrogen containing plasmas, such as N-plasma, atoms, or radicals or N and H containing plasma, atoms, or radicals.

In some embodiments a W sulfide thin film may be formed on a substrate by an ALD type process comprising at least one deposition cycle comprising:

contacting the surface of a substrate with vaporized W(IV) beta-diketonate precursor to form at most a molecular monolayer of W containing species on the substrate;

removing excess W(IV) beta-diketonate precursor and reaction by products, if any, from the surface;

contacting the surface of the substrate with an precursor comprising sulfur; and removing from the surface excess precursor comprising sulfur and any gaseous by-products formed in the reaction between the W containing species layer and the precursor comprising silicon.

The contacting and removing steps can be repeated until a W sulfide thin film of the desired thickness has been formed.

In some embodiments suitable precursors comprising sulfur may include H$_2$S or (CH$_3$)$_2$S, among other.

In some embodiments a W containing material may be formed on a substrate by a process comprising at least one deposition cycle, the deposition cycle comprising alternately and sequentially contacting the substrate with a vapor phase W precursor and a vapor phase second precursor. In some embodiments the deposition cycle may be repeated two or more times. In some embodiments the deposition cycle may be repeated two or more times sequentially. In some embodiments excess W precursor and reaction byproducts, if any, may be removed subsequent to contacting the substrate with a vapor phase W precursor and prior to contacting the substrate with the vapor phase second precursor. In some embodiments excess second precursor and reaction byproducts, if any, may be removed subsequent to contacting the substrate with a vapor phase second precursor and prior to beginning another deposition cycle. In some embodiments the substrate may be contacted with a purge gas subsequent to contacting the substrate with the W vapor phase precursor and prior to contacting the substrate with the vapor phase second precursor. In some embodiments the substrate may be contacted with a purge gas subsequent to contacting the substrate with the second vapor phase precursor prior to beginning another deposition cycle.

Synthesis of W(IV) Beta-Diketonate Precursors

Methods are provided for making the W precursors used in the vapor deposition processes described herein. In some embodiments precursors are synthesized having a formula of W(L)$_4$, wherein L is a beta-diketonato ligand, such as acac, tfac, hfac, fod or thd. In some embodiments the W precursor that is synthesized has a formula of W(thd)$_4$.

In some embodiments all handling and manipulation may be carried out in an atmosphere that does not comprise air, oxygen, or moisture. In some embodiments all handling and manipulation may be carried out in an inert gas atmosphere, for example a N$_2$ or Ar atmosphere.

Figure 2:
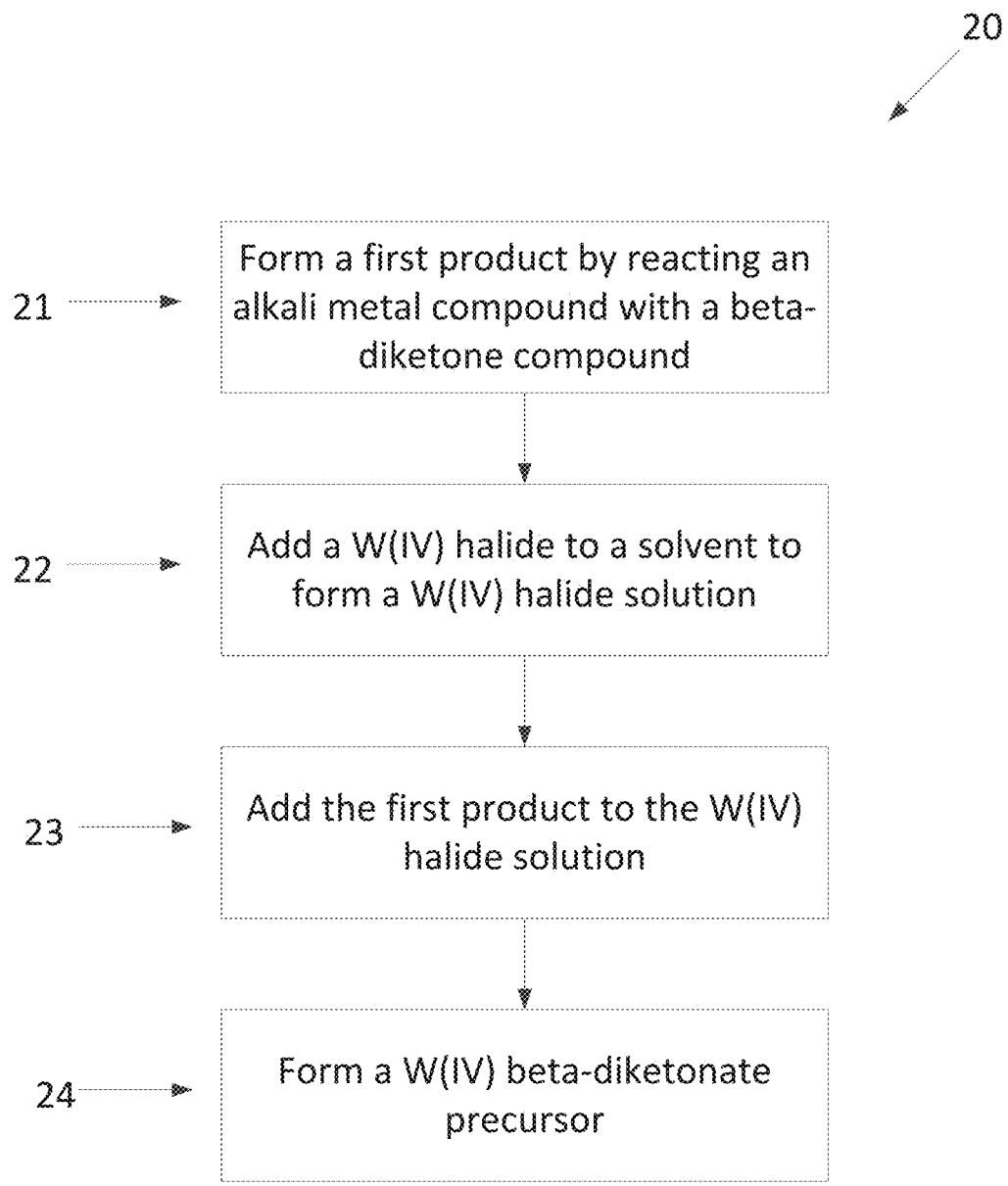
FIG. 2 is a process flow diagram generally illustrating a method for synthesizing a W(IV) beta-diketonate precursor.

FIG. 2 is a process flow diagram generally illustrating methods for forming W(IV) beta-diketonate precursors 20. In some embodiments the process for making a W(IV) beta-diketonate precursor comprises:

forming a first product by reacting an alkali metal compound with a beta-diketone compound in a solvent at step 21;

adding a W(IV) halide to a solvent at step 22 to form a W(IV) halide solution;

subsequently adding the first product to the W(IV) halide solution at step 23, thereby forming a W(IV) beta-diketonate precursor at step 24 having the formula W(L)$_4$, wherein L is a beta-diketonato ligand.

In some embodiments the alkali metal compound of step 21 may comprise, for example KH, NaH, BuLi, or MeLi. In some embodiments the alkali metal compound of step 21 is potassium hydride (KH). In some embodiments the alkali metal compound may be added to a solvent. In some embodiments the solvent may comprise a heterocyclic solvent. In some embodiments the solvent is THF.

In some embodiments the beta-diketone compound of step 21 may comprise Hthd; Hacac; Htfac, where Htfac is trifluoroacetylacetone; Hfod, where fod is 2,2-dimethyl-6,6,7,7,8,8,8-heptafluoro-3,5-octanedione; or Hhfac, where Hhfac is hexafluoroacetylacetone. In some embodiments reacting an alkali metal compound with a beta-diketone compound may comprise adding the beta-diketone compound, or a mixture comprising the beta-diketone compound, to the solution comprising the alkali metal compound to thereby form a first product having the formula M$^1$L, wherein M$^1$ is an alkali metal and L is a beta-diketonato ligand. In some embodiments KH is added to THF to form a solution. Hthd is then added to the solution to react with the KH and thereby form a first product comprising K(thd).

In some embodiments the solution may be stirred until the reaction is complete. In some embodiments the mixture is stirred for a first duration. In some embodiments any gaseous by-products produced by the reaction may be exhausted, for example through a bubbler, such as a mercury bubbler.

In some embodiments the W(IV) halide of step 22 is an anhydrous W(IV) halide. In some embodiments the W(IV) halide of step 22 has the formula WX$_4$, wherein X is a halide, for example Cl. In some embodiments the solvent of step 22 may comprise a heterocyclic solvent. In some embodiments the solvent of step 22 is THF. Thus, in some embodiments WCl$_4$ is added to THF at step 22. In some embodiments the solvent is optionally cooled prior to, during, and/or after the W(IV) halide is added. In some embodiments the solvent, for example THF may be cooled prior to the addition of the W(IV) halide compound.

In some embodiments approximately 4 equivalents of the first product are added to 1 equivalent of the product(IV) halide solution, thereby forming a W(IV) beta-diketonate precursor having the formula ML$_4$, wherein L is a beta-diketonato ligand. In some embodiments the W(IV) halide solution may be cooled prior to the addition of the first product. In some embodiments, after the addition of the first product, the mixture is allowed to warm to room temperature. In some embodiments the mixture is stirred for a second duration. In some embodiments the mixture is stirred until the reaction is complete.

After the reaction is substantially complete, the final product is separated and isolated from any solvents, by-products, excess reactants, or any other compounds that are not desired in the final product.

In some embodiments a W(IV) beta-diketonate precursor may be formed by reacting a W(IV) halide with a compound comprising a beta-diketonato ligand. In some embodiments the compound comprising a beta-diketanato ligand may have the formula M$^1$L, wherein M$^1$ is an alkali metal and L is a beta-diketonato ligand. In some embodiments a W(IV) beta-diketonate precursor may be formed by adding a compound comprising a beta-diketonato ligand to a solution comprising a W(IV) halide such that the compounds react to form a W(IV) beta-diketonate precursor. In some embodiments a W(IV) beta-diketonate precursor may be formed by adding a W(IV) halide to a solution comprising a compound comprising a beta-diketonato ligand such that the compounds react to form a W(IV) beta-diketonate precursor. In some embodiments a W(IV) halide compound and a compound comprising a W(IV) beta-diketonato ligand may simultaneously, or substantially simultaneously be added to a solvent such that they react to form a W(IV) beta-diketonate precursor. In some embodiments one or more of the compounds and or solvents may be cooled before or during the reaction process.

In some embodiments the process for making a W(IV) beta-diketonate precursor comprises:

forming a first product by reacting KH with Hthd in THF at step 21;

adding a WCl$_4$ to THF at step 22 to form a WCl$_4$ solution;

subsequently adding the first product to the WCl$_4$ solution at step 23, thereby forming a W(IV) beta-diketonate precursor at step 24 having the formula W(thd)$_4$.

EXAMPLE 1

W(thd)$_4$ was synthesized by the following process. All handling and manipulation was done under the rigorous exclusion of air and moisture using standard Schlenk techniques and an inert gas (N$_2$ or Ar) glove box.

First, 4.59 g (114.44 mmol) of potassium hydride (KH) was added to 100 ml of tetrahydrofuran (THF). A stoichiometric amount, 21.09 g (114.44 mmol), of 2,2,6,6-tetramethylheptane-3,5-dione (Hthd) was added to 100 ml of THF. The Hthd dissolved in 100 ml of THF was added dropwise to the KH and THF mixture while stirring. Evolved H$_2$ gas released during the procedure was released through a mercury bubbler. The resultant mixture was stirred for 4 hours at room temperature to form a potassium 2,2,6,6-tetramethylheptane-3,5-dione (K(thd)) solution.

9.32 g (28.61 mmol) of WCl$_4$ was suspended in 200 ml of THF and cooled to −10° C. The prepared K(thd) solution was added to the suspension of WCl$_4$ while stirring using Ar pressure and a Teflon cannula. This mixture was allowed to warm to room temperature and was stirred overnight. The mixture was evaporated until dry, leaving a black residue that was transferred to a sublimator and sublimed out at a temperature of 210° C. and a pressure of 0.5 mbar. The resultant W(thd)$_4$ sublimate was collected in the glove box.

The synthesized compound was analyzed using mass spectrometry. A molecular ion with an isotopic pattern corresponding to [W(thd)$_4$]$^+$ was seen at m/z 917. In addition to molecular ion [W(thd)$_4$]$^+$, [W(thd)$_3$]$^+$ and other fragment ions, several peaks corresponding to fragment ions with oxygen, such as [W(thd)$_3$O]$^+$, [W(thd)$_2$(OH)$_3$]$^+$, and [W(thd)$_2$O$_2$]$^+$, can be seen. However, these oxygen containing peaks are likely due to exposure of the W(thd)$_4$ compound to air during sample loading into the mass spectrometer.

Figure 3:
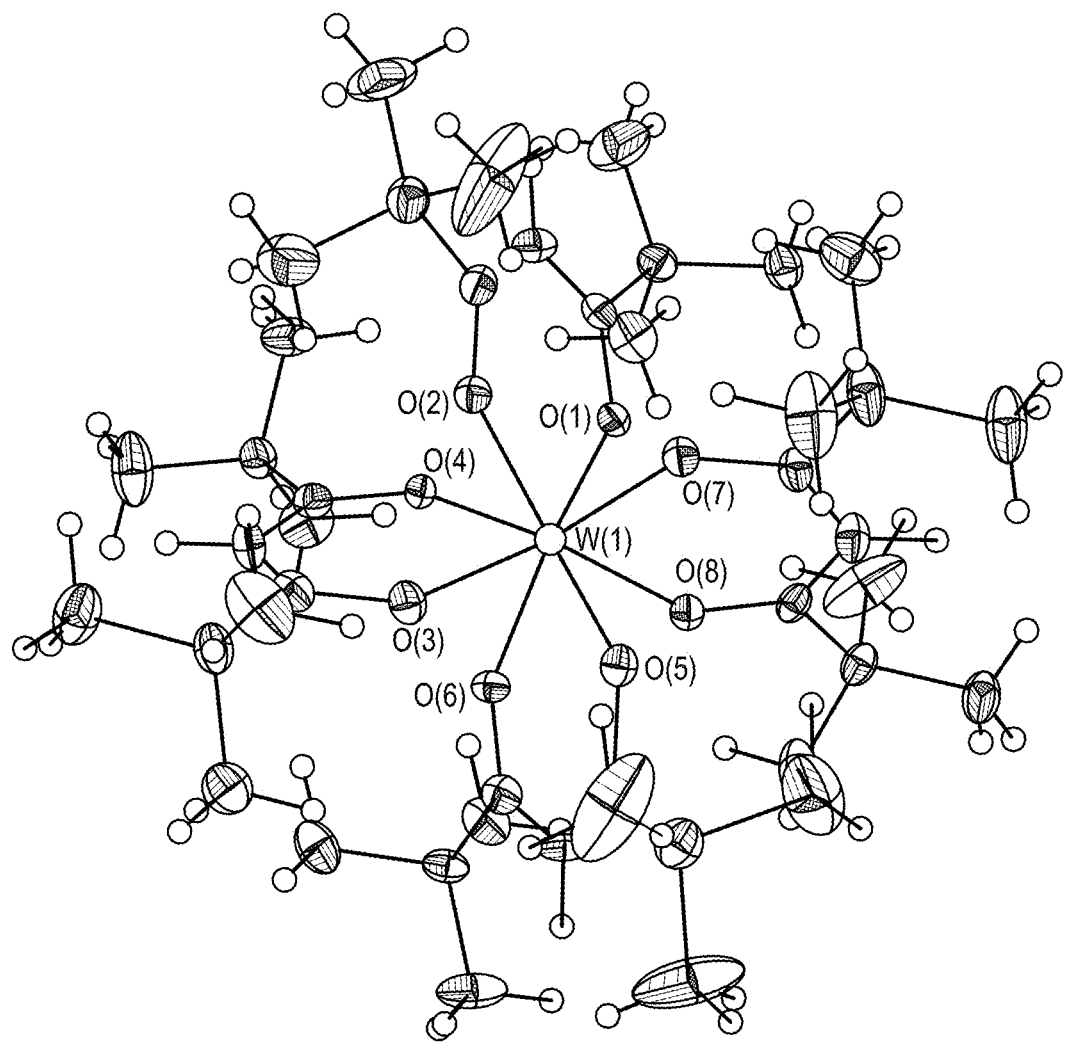
FIG. 3 illustrates the molecular structure of a $W(thd)_4$ as determined by single crystal x-ray diffraction.

The molecular structure of the synthesized compound was analyzed using single crystal x-ray diffraction (SCXRD). The structure of the synthesized W(thd)$_4$ compound is illustrated in FIG. 3.

Figure 4:
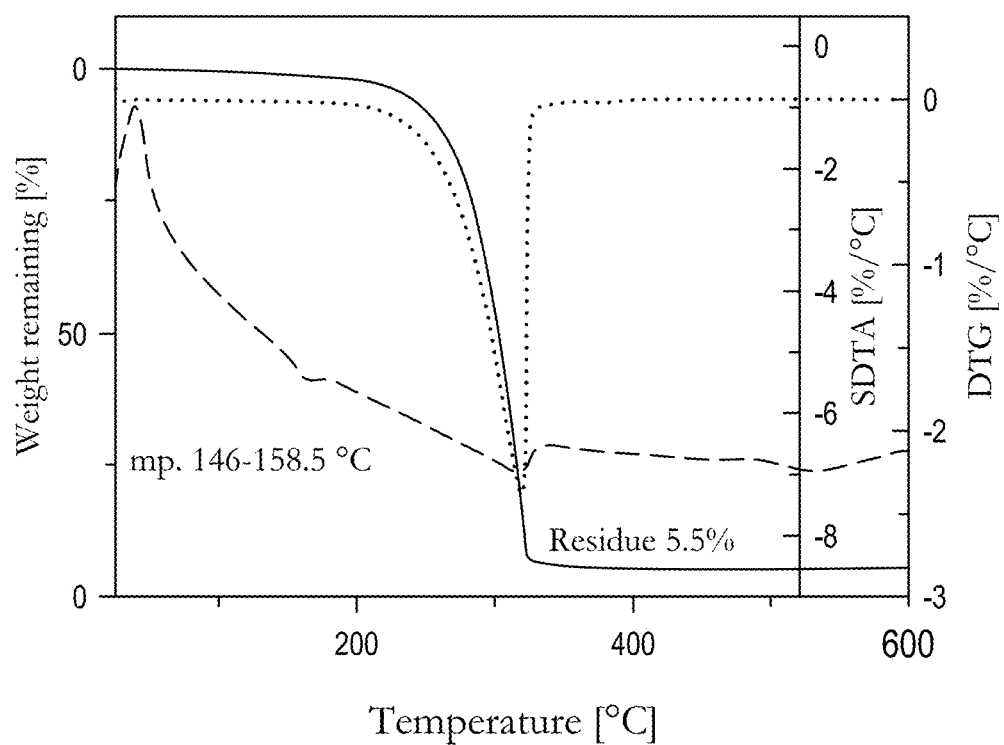
FIG. 4 illustrates thermoanalytical measurement results, that is, TGA, DTG and SDTA curves for $W(thd)_4$.

The thermal properties of W(thd)$_4$ were investigated using thermogravimetric analysis (TGA). As shown in FIG. 4, thermogravimetric (TG), derivative thermogravimetric (DTG), and single differential thermal analysis (SDTA) curves for W(thd)$_4$ show a single step evaporation of the compound at about 220° C. to 330° C. The curves also show a 5.5% residue at 600° C. However, in some embodiments, there may be less than 5.5% residue at 600° C., for example, less than 5% residue, less that 4% residue, less than 3% residue, less than 2% residue, or less than 1% residue or lower.

Second Precursors

It will be understood by one skilled in the art that any number of second precursors may be used in the vapor deposition processes disclosed herein, depending on the desired W containing film to be deposited. In some embodiments a second precursor may be an oxygen precursor, or oxygen containing reactant. In some embodiments a second precursor may be a nitrogen precursor, or nitrogen containing reactant. In some embodiments a second precursor may be a chalcogen precursor, or chalcogen containing reactant. In some embodiments the second precursor may not significantly contribute material to the final formed film.

In some embodiments an oxygen precursor may comprise, for example, $O_2$, $H_2O$, $O_3$, and/or other oxygen-containing compounds. In some embodiments an oxygen precursor may comprise oxygen plasma, oxygen radicals, or oxygen atoms. In some embodiments a nitrogen precursor may comprise, for example, $N_2$, $NO_2$, $NH_3$, and/or other nitrogen containing compounds. In some embodiments the nitrogen precursor may comprise nitrogen plasma, nitrogen radicals, or nitrogen atoms.

It will be understood by one skilled in the art that any number of chalcogen precursors may be used in the vapor deposition processes disclosed herein. In some embodiments, a chalcogen precursor is selected from the following list: $H_2S$, $H_2Se$, $H_2Te$, $(CH_3)_2S$, $(NH_4)_2S$, dimethylsulfoxide $((CH_3)_2SO)$, $(CH_3)_2Se$, $(CH_3)_2Te$, elemental or atomic S, Se, Te, other precursors containing chalcogen-hydrogen bonds, such as $H_2S_2$, $H_2$—$Se_2$, $H_2Te_2$, or chalcogenols with the formula R-E-H, wherein R can be a substituted or unsubstituted hydrocarbon, for example a $C_1$-$C_8$ alkyl or substituted alkyl, such as an alkylsilyl group, or a linear or branched $C_1$-$C_5$ alkyl group, and E can be S, Se, or Te. In some embodiments a chalcogen precursor is a thiol with the formula R—S—H, wherein R can be a substituted or unsubstituted hydrocarbon, such as a $C_1$-$C_8$ alkyl group, or a linear or branched $C_1$-$C_5$ alkyl group. In some embodiments a chalcogen precursor has the formula $(R_3Si)_2E$, wherein $R_3Si$ is an alkylsilyl group and E can be S, Se, or Te. In some embodiments, a chalcogen precursor comprises S or Se. In some embodiments, a chalcogen precursor comprises S. In some embodiments the chalcogen precursor may comprise an elemental chalcogen, such as elemental sulfur. In some embodiments, a chalcogen precursor does not comprise Te. In some embodiments, a chalcogen precursor does comprise Se. In some embodiments, a chalcogen precursor is selected from precursors comprising S, Se or Te. In some embodiments, a chalcogen precursor comprises $H_2S_n$, wherein n is from 4 to 10.

Suitable chalcogen precursors may include any number of chalcogen-containing compounds so long as they include at least one chalcogen-hydrogen bond. In some embodiments the chalcogen precursor may comprise a chalcogen plasma, chalcogen atoms or chalcogen radicals. In some embodiments where an energized chalcogen precursor is desired, a plasma may be generated in the reaction chamber or upstream of the reaction chamber. In some embodiments the chalcogen precursor does not comprise an energized chalcogen precursor, such as plasma, atoms or radicals. In some embodiments the chalcogen precursor may comprise a chalcogen plasma, chalcogen atoms or chalcogen radicals formed from a chalcogen precursor comprising a chalcogen-hydrogen bond, such as $H_2S$. In some embodiments a chalcogen precursor may comprise a chalcogen plasma, chalcogen atoms or chalcogen radicals such as a plasma comprising sulfur, selenium or tellurium. In some embodiments the plasma, atoms or radicals comprise tellurium. In some embodiments the plasma, atoms or radicals comprise selenium.

EXAMPLE 2

$WS_2$ thin films were deposited according to ALD processes described herein at 300° C., 350° C., and 500° C. A F120 ALD reactor (ASM Microchemistry) was used to deposit the $WS_2$ films. $W(thd)_4$ was used as the W precursor and $H_2S$ was used a second precursor. Sample $WS_2$ films were deposited on silicon, $Al_2O_3$, and ZnS substrates. The $WS_2$ sample films were deposited using an ALD process including 2000 deposition cycles, with each cycle having a W precursor pulse time of 1 second and a second precursor pulse time of 2 seconds, separated by 1 second nitrogen purges. The $W(thd)_4$ was evaporated from an open glass boat that was heated to between 160° C. and 165° C. inside the reactor.

Energy dispersive X-ray spectrometry (EDX) was used to analyze the films and it was found that the films contained W and S. No indications of the presence of crystalline material were found when the films were analyzed using X-ray diffraction (XRD).

Figure 5A:
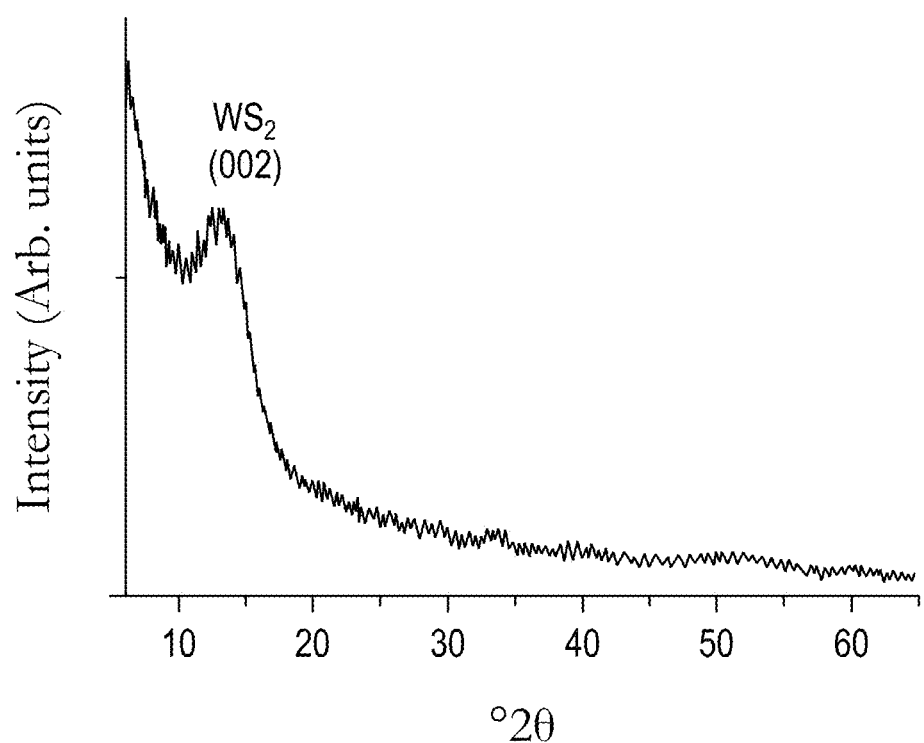
FIG. 5A is an X-ray diffractogram of a $WS_2$ film formed at 350° C. according to some embodiments.
Figure 5B:
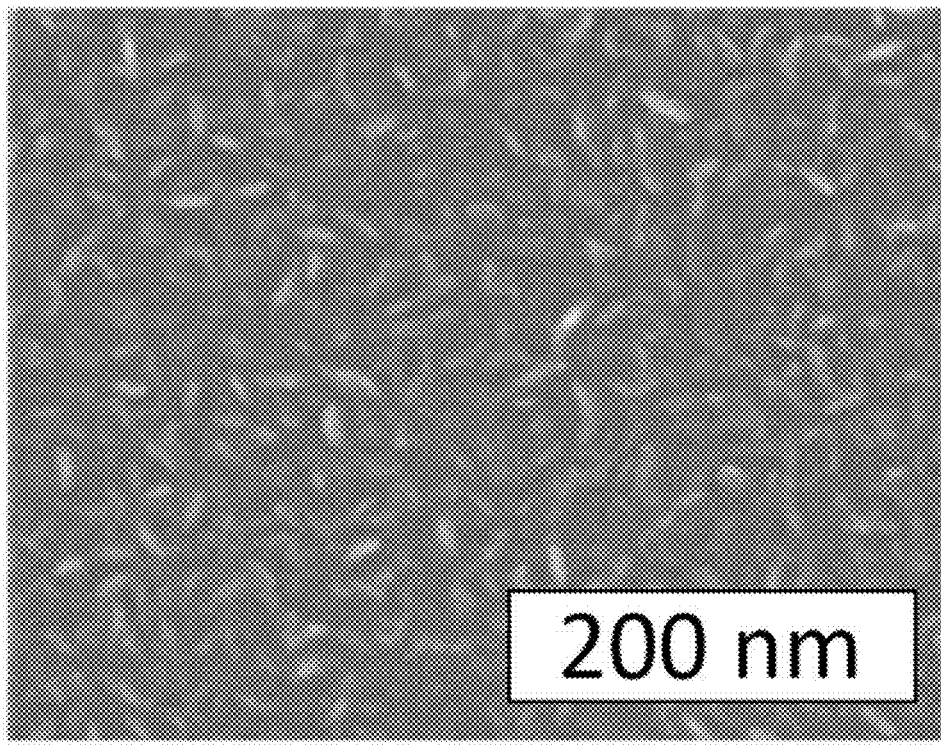
FIG. 5B is a scanning electron microscope (SEM) image of a $WS_2$ film formed at 350° C. according to some embodiments.

The sample films deposited at 350° C. were also analyzed using XRD. As shown in FIG. 5A, these sample films showed a broad peak centered near 13° (2θ) that was identified as $WS_2$. The crystallinity of these sample $WS_2$ films was confirmed via scanning electron microscopy. As shown in FIG. 5B, flakes of crystalline $WS_2$ were observed on the substrate. Some slight decomposition of $W(thd)_4$ was observed inside the reactor subsequent to film deposition. Film samples deposited at between 300° C. and 350° C. had an estimated thickness of about 2 nm, as calculated from EDX data.

Figure 6A:
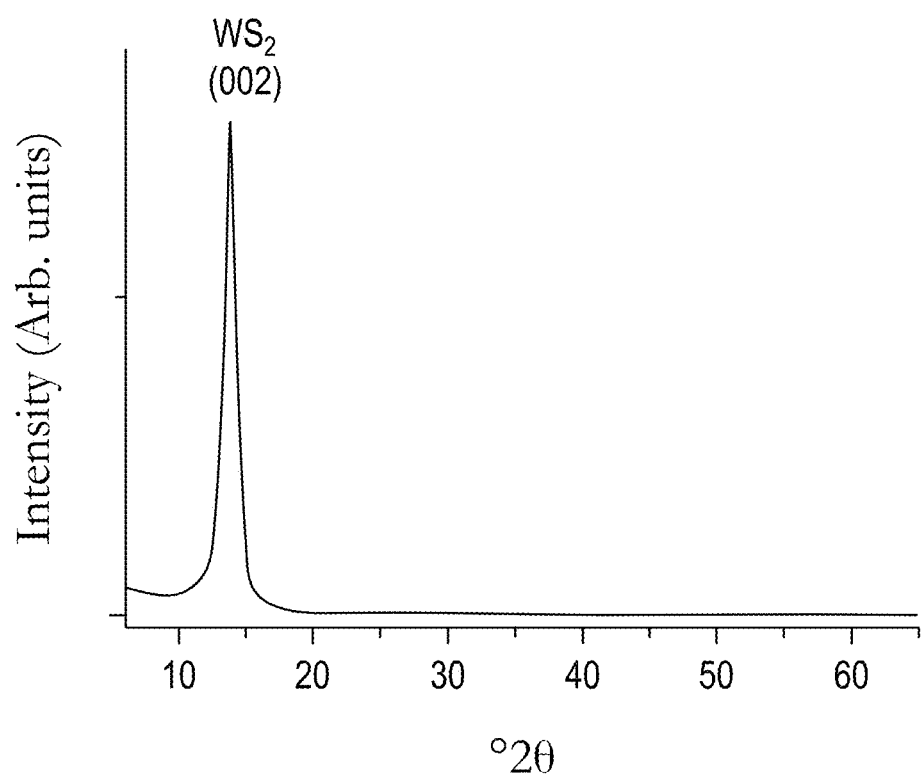
FIG. 6A is an X-ray diffractogram of a $WS_2$ film formed at 500° C. according to some embodiments.
Figure 6B:
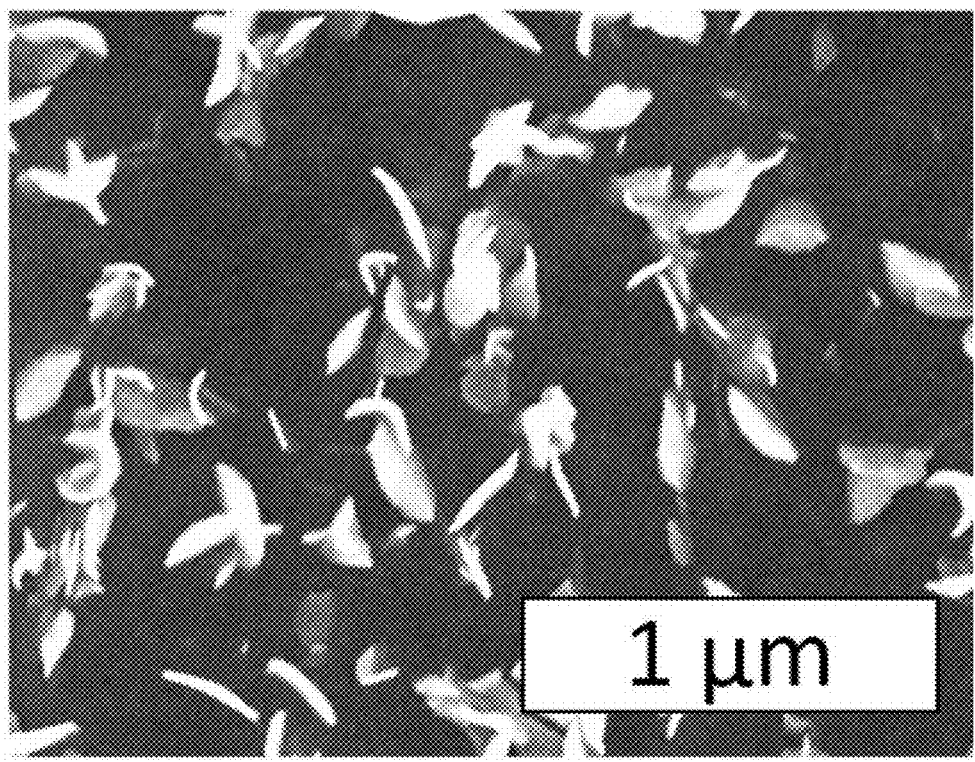
FIG. 6B is a scanning electron microscope (SEM) image of a $WS_2$ film formed at 500° C. according to some embodiments.

A $WS_2$ film sample deposited at 500° C. and according to the parameters described above, but including a 0.2 second W precursor pulse time were crystalline, although decomposition of $W(thd)_4$ did occur. As illustrated in FIG. 6A, XRD analysis showed a high intensity peak identified as crystalline $WS_2$. The sample film was found to be about 10 nm thick. A shown in FIG. 6B, SEM analysis revealed large thin crystalline flake. Some of the flakes were observed to be perpendicular to the substrate with lateral dimensions on the order of 200 nm. The sample film composition was determined via EDX and was found to be 32 at % W, and 68 at % S, which was within the experimental error for the theoretical values for $WS_2$ (33.3 at % W, 66.6 at % S).

2D Materials

The vapor deposition processes described herein may be used to deposit 2D materials comprising W, for example W dichalcogenides such as $WS_2$ or $WSe_2$ 2D materials. 2D materials, also referred to as single layer materials, are materials that consist of a single connected molecular monolayer. While 2D materials form a single connected molecular monolayer, multiple monolayers may be deposited by the deposition processes disclosed herein. For example, in the case of 2D $WS_2$, the 2D material comprises a single layer of covalently bonded $WS_2$ molecules, arranged so that one layer of W atoms is sandwiched between two layers of S atoms. The basic atomic structure of a $WS_2$ will be familiar to the skilled artisan.

Due to their unusual characteristics, 2D materials are useful in a wide variety of potential applications, for example as lubrication, in optoelectronics, spintronics and valleytronics, in THz generation and detection, for use as catalysts, chemical and biological sensors, supercapacitors, LEDs, solar cells, Li-ion batteries, and as MOSFET channel materials.

Unlike other 2D materials such as graphene, 2D W dichalcogenides possess unique electronic properties that make them useful for semiconductor device miniaturization. For example, unlike graphene, 2D W dichalcogenides have a direct band gap and are semiconducting. Therefore, W dichalcogenides are useful in electronic devices, for example W dichalcogenides can be used as a channel material in a gate stack or transistors.

According to some embodiments a 2D material comprising W can be deposited by vapor deposition according to the methods disclosed herein. In some embodiments a 2D material comprising W may comprise less than or equal to ten molecular monolayers of a compound comprising W, less than 5 molecular monolayers, or less than or equal to 3 molecular monolayers.

In some embodiments the 2D material comprising W may comprise less than or equal to ten molecular monolayers of a W dichalcogenide, less than 5 molecular monolayers, or less than or equal to 3 molecular monolayers. In some embodiments the 2D material comprising W may comprise less than or equal to ten molecular monolayer of $WS_2$, $WSe_2$, or $WTe_2$, less than 5 molecular monolayers, or less than or equal to 3 molecular monolayers.

In some embodiments a method for depositing a 2D material comprising W on a substrate may comprise a deposition process as disclosed herein comprising multiple cycles. In some embodiments a method for depositing a 2D material comprising W may comprise at least one deposition cycle, up to about 500 deposition cycles, up to about 200 deposition cycles, or up to about 100 deposition cycles. As can be selected by the skilled artisan depending on the particular precursors, substrate and process conditions, a method for depositing a 2D material comprising W on a substrate may comprise an ALD process as disclosed herein comprising less than or equal to 50 cycles, less than or equal to 25 cycles, less than or equal to 15 cycles, or less than or equal to 10 cycles.

In some embodiments the deposited 2D material comprising W may be less than 10 nm, less than 5 nm, less than 3 nm, less than 2 nm, less than 1.5 nm, or less than 1.0 nm.

In some embodiments material comprising W, such as a 2D material, is able to be used in an electronic device, for example as the channel material in a gate stack. In some embodiments a material comprising W, such as a 2D material, may be deposited after the gate dielectric, that is, channel-last. In some embodiments a material comprising W, such as a 2D material, may be deposited prior to the gate dielectric, that is, channel-first. In some embodiments the gate stack may be manufactured upside down, such that the channel is above the gate in the gate stack.

As used herein, the term "about" may refer to a value that is within 15%, within 10%, within 5%, or within 1% of a given value.

The terms "film" and "thin film" are used herein for simplicity. "Film" and "thin film" are meant to mean any continuous or non-continuous structures and material deposited by the methods disclosed herein. For example, "film" and "thin film" could include 2D materials, nanorods, nanotubes or nanoparticles or even single partial or full molecular layers or partial or full atomic layers or clusters of atoms and/or molecules. "Film" and "thin film" may comprise material or layer with pinholes, but still be at least partially continuous.

The term chalcogen as used herein is meant to refer primarily to the chemical elements sulfur, selenium, and tellurium, although in some cases, as will be clear to those of ordinary skill in the art the term may also refer to oxygen. Similarly, the terms chalcogenide and dichalcogenide are mean to refer primarily to sulfides, selenides, and tellurides, although in some cases, as will be clear to those of ordinary skill in the art such terms may also refer to oxides.

It will be understood by those of skill in the art that numerous and various modifications can be made without departing from the spirit of the present invention. The described features, structures, characteristics and precursors can be combined in any suitable manner. Therefore, it should be clearly understood that the forms of the present invention are illustrative only and are not intended to limit the scope of the present invention. All modifications and changes are intended to fall within the scope of the invention, as defined by the appended claims.

What is claimed is:

1. A process for forming a W containing thin film on a substrate in a reaction chamber comprising at least one deposition cycle, the deposition cycle comprising:
   contacting the substrate with a vapor phase W precursor, wherein the W in the W precursor has an oxidation state of +IV, such that W containing species adsorb on a surface of the substrate;
   contacting the substrate with a vapor phase second precursor, wherein the second precursor reacts with the W containing species on the surface of the substrate.

2. The process of claim 1, wherein the deposition cycle further comprises removing excess W precursor and reaction byproducts, if any, after contacting the substrate with the vapor phase W precursor.

3. The process of claim 1, wherein the deposition cycle further comprises removing excess second precursor and reaction byproducts, if any, after contacting the substrate with the vapor phase second precursor.

4. The process of claim 1, wherein the process comprises repeating the deposition cycle two or more times.

5. The process of claim 1, wherein the process is an atomic layer deposition (ALD) process.

6. The process of claim 1, wherein the process is a chemical vapor deposition (CVD) process.

7. The process of claim 1, wherein the W precursor is a W(IV) beta-diketonate.

8. The process of claim 7, wherein the W precursor is W(IV) 2,2,6,6-tetramethyl-3,5-heptanedionate $(W(thd)_4)$.

9. The process of claim 1, wherein the W containing thin film comprises a W sulfide, W selenide, or W telluride thin film.

10. The process of claim 9, wherein the second precursor comprises a chalcogenide.

11. The process of claim 10, wherein the second precursor comprises $H_2S$, $H_2Se$, $H_2Te$, $(CH_3)_2S$, $(CH_3)_2Se$, or $(CH_3)_2Te$.

12. The process of claim 1, wherein the W containing thin film comprises a W nitride thin film.

13. The process of claim 12, wherein the second precursor comprises nitrogen.

14. The process of claim 13, wherein the second precursor comprises $N_2$, $NO_2$, or $NH_3$.

15. The process of claim 1, wherein the W containing thin film comprises a W oxide thin film.

16. The process of claim 15, wherein the second precursor comprises oxygen.

17. The process of claim 16, wherein the second precursor comprises $O_2$, $H_2O$, or $O_3$.

18. The process of claim 1, wherein the second precursor comprises a plasma.

19. The process of claim 1, wherein the W containing thin film comprises a 2D material.

20. The process of claim 19, wherein the W containing thin film comprises less than or equal to ten molecular monolayers of a W dichalcogenide.

\* \* \* \* \*